(12) United States Patent
Cao et al.

(10) Patent No.: US 11,202,860 B2
(45) Date of Patent: Dec. 21, 2021

(54) CONTROLLED DRUG DELIVERY IN POINT-OF-CARE DRUG DELIVERY SYSTEM BASED ON REAL-TIME MONITORING WITH INTEGRATED SENSOR

(71) Applicant: International Business Machines Corporation, Armonk, NY (US)

(72) Inventors: Qing Cao, Westchester, NY (US); Shu-Jen Han, Cortlandt Manor, NY (US); Jianshi Tang, Elmsford, NY (US); Bharat Kumar, Tarrytown, NY (US)

(73) Assignee: International Business Machines Corporation, Armonk, NY (US)

( * ) Notice: Subject to any disclaimer, the term of this patent is extended or adjusted under 35 U.S.C. 154(b) by 230 days.

(21) Appl. No.: 16/001,391

(22) Filed: Jun. 6, 2018

(65) Prior Publication Data

US 2019/0374712 A1    Dec. 12, 2019

(51) Int. Cl.
*A61M 5/168* (2006.01)
*A61M 5/172* (2006.01)
*A61B 5/00* (2006.01)

(52) U.S. Cl.
CPC .............. *A61M 5/1723* (2013.01); *A61B 5/68* (2013.01); *A61B 5/6801* (2013.01);
(Continued)

(58) Field of Classification Search
CPC ................ A61M 5/1723; A61M 37/00; A61M 2005/14208; A61M 5/168;
(Continued)

(56) References Cited

U.S. PATENT DOCUMENTS 5,750,138 A     5/1998  Saaman et al.
2005/0025820 A1*  2/2005  Kester ................. A61K 9/1272
                                             424/450
(Continued)

FOREIGN PATENT DOCUMENTS

CN         203506974 U       4/2014
WO        2014161036 A1     10/2014
WO  PCT/IB2019/053919       9/2019

OTHER PUBLICATIONS

Y. Wang et al., All Solid-State pH Electrode Based on Titanium Nitride Sensitive Film, 2006, Electroanalysis, 18, No. 15, pp. 1493-1498 (Year: 2006).*

(Continued)

*Primary Examiner* — Nathan R Price
*Assistant Examiner* — Anna E Goldberg-Richmeier
(74) *Attorney, Agent, or Firm* — Stosch Sabo; Ryan, Mason & Lewis, LLP

(57) ABSTRACT

A drug delivery system includes a substrate, an integrated sensor disposed on the substrate, a drug delivery element disposed on the substrate, and a control unit coupled to the integrated sensor and the drug delivery element. The integrated sensor includes first and second electrodes disposed on a first surface of the substrate. The drug delivery element includes a reservoir disposed on the first surface of the substrate, a thermally active polymer enclosing the reservoir, and a heating coil disposed over the thermally active polymer. The control unit is configured to measure a biological parameter by measuring a voltage difference between the first and second electrodes of the integrated sensor, and to apply a trigger signal to the heating coil of the drug delivery element responsive to the measured biological parameter indicating a designated condition to heat up the
(Continued)

thermally active polymer to selectively release a drug from the reservoir.

20 Claims, 8 Drawing Sheets

(52) U.S. Cl.
CPC ............... *A61M 2005/1726* (2013.01); *A61M 2205/3553* (2013.01); *A61M 2205/3561* (2013.01); *A61M 2205/364* (2013.01); *A61M 2230/208* (2013.01)

(58) Field of Classification Search
CPC .... A61M 2005/1726; A61M 2230/208; A61B 5/14; A61B 5/6833; A61B 5/68; A61B 5/6801
See application file for complete search history.

(56) References Cited

U.S. PATENT DOCUMENTS

| | | | | |
|---|---|---|---|---|
| 2008/0064980 | A1* | 3/2008 | Lee | A61B 5/02405 600/547 |
| 2010/0106076 | A1 | 4/2010 | Nisato et al. | |
| 2014/0037746 | A1 | 2/2014 | Ashton et al. | |
| 2014/0336487 | A1* | 11/2014 | Wang | A61B 5/1473 600/352 |
| 2015/0073295 | A1 | 3/2015 | Gordon et al. | |
| 2018/0263539 | A1* | 9/2018 | Javey | A61B 5/14539 |
| 2018/0368745 | A1* | 12/2018 | Cahan | A61B 5/14539 |
| 2019/0247649 | A1* | 8/2019 | Chang | B32B 37/12 |
| 2019/0388667 | A1* | 12/2019 | Xu | A61N 1/0428 |

OTHER PUBLICATIONS

H.Y.Y. Nyein et al., "A Wearable Electrochemical Platform for Noninvasive Simultaneous Monitoring of Ca2+ and pH," ACS Nano, Jul. 5, 2016, pp. 7216-7224, vol. 10, No. 7.
D.-H. Kim et al., "Epidermal Electronics," Science, Aug. 12, 2011, pp. 838-843, vol. 333, No. 6050.
W. Gao et al., "Fully Integrated Wearable Sensor Arrays for Multiplexed In Situ Perspiration Analysis," Nature, Jan. 28, 2016, pp. 509-514, vol. 529, No. 7587.
R. Gurrala et al., "Novel pH Sensing Semiconductor for Point-of-Care Detection of HIV-1 Viremia," Scientific Reports, Nov. 10, 2016, 6 pages, vol. 6, No. 36000.
S. Ono et al., "Increased Wound pH as an Indicator of Local Wound Infection in Second Degree Burns," Jun. 2015, pp. 820-824, vol. 41, No. 4.
H. Lee et al., "A Graphene-Based Electrochemical Device with Thermoresponsive Microneedles for Diabetes Monitoring and Therapy," Nature Nanotechnology, Jun. 1, 2016, pp. 566-572, vol. 11, No. 6.
B. Mirani et al., "An Advanced Multifunctional Hydrogel-Based Dressing for Wound Monitoring and Drug Delivery," Advanced Healthcare Matererials, Oct. 2017, 15 pages, vol. 6, No. 19.

\* cited by examiner

400

450

CONTROLLED DRUG DELIVERY IN POINT-OF-CARE DRUG DELIVERY SYSTEM BASED ON REAL-TIME MONITORING WITH INTEGRATED SENSOR

BACKGROUND

The present application relates to biological monitoring, and more specifically, to techniques for drug delivery based on biological monitoring. Real-time monitoring of subjects, such as human subjects, provides various advantages. For example, various illnesses afflicting subjects may require continuous monitoring in order to provide timely and effective treatment thereof. As another example, wounds of a subject may require continuous monitoring in order to provide timely and effective treatment thereof, such as to prevent infection of a wound.

SUMMARY

Embodiments of the invention provide techniques for controlled drug delivery using a point-of-care drug delivery system having one or more sensors integrated therewith for real-time monitoring of a target site.

In one embodiment, a drug delivery system comprises a substrate, at least one integrated sensor disposed on the substrate, at least one drug delivery element disposed on the substrate, and a control unit coupled to the at least one integrated sensor and the at least one drug delivery element. The at least one integrated sensor comprises a first electrode disposed on a first surface of the substrate and at least a second electrode disposed on the first surface of the substrate. The at least one drug delivery element comprises a reservoir disposed on the first surface of the substrate, a thermally active polymer enclosing the reservoir and a heating coil disposed over the thermally active polymer. The control unit is configured to measure at least one biological parameter of a subject by measuring a voltage difference between the first electrode and the second electrode of the at least one integrated sensor, and to apply a trigger signal to the heating coil of the at least one drug delivery element responsive to the measured at least one biological parameter indicating a designated condition, the trigger signal heating up the thermally active polymer to selectively release a drug from the reservoir.

In another embodiment, an apparatus comprises a memory and a processor coupled to the memory and configured to measure at least one biological parameter of a subject by measuring a voltage difference between a first electrode and a second electrode of at least one integrated sensor disposed on a substrate, and to apply a trigger signal to a heating coil of at least one drug delivery element disposed on the substrate responsive to the measured at least one biological parameter indicating a designated condition, the trigger signal heating up a thermally active polymer of the at least one drug delivery element that encloses a reservoir to selectively release a drug from the reservoir.

In another embodiment, a method for controlled drug delivery comprises measuring at least one biological parameter of a subject by measuring a voltage difference between a first electrode and a second electrode of at least one integrated sensor disposed on a substrate, and applying a trigger signal to a heating coil of at least one drug delivery element disposed on the substrate responsive to the measured at least one biological parameter indicating a designated condition, the trigger signal heating up a thermally active polymer of the at least one drug delivery element that encloses a reservoir to selectively release a drug from the reservoir. The method is performed by a control unit comprising a processor coupled to a memory.

DETAILED DESCRIPTION

Illustrative embodiments of the invention may be described herein in the context of illustrative methods for controlled drug delivery using a point-of-care drug delivery system with integrated sensing capability, along with apparatus, systems and devices for such a point-of-care drug delivery system. However, it is to be understood that embodiments of the invention are not limited to the illustrative methods, apparatus, systems and devices but instead are more broadly applicable to other suitable methods, apparatus, systems and devices.

A variety of illnesses and wounds may require continuous monitoring so as to provide timely and efficient treatment thereof. Integrated biological sensors (biosensors) can provide fast and accurate point-of-care testing, and when integrated with a precise drug delivery means enable effective real-time treatment. Point-of-care testing is useful in various scenarios. For example, open wounds on human skin may cause measurable, in some cases dramatic, changes in measured parameters such as local pH value, body temperature, etc. Such changes may be used for infection monitoring, and for appropriate drug delivery (e.g., antibiotics) in response to such changes. Drug delivery may be implemented once clinical signs of infection or other designated conditions are detected. Changes in some parameters, such as local pH value, may be detected prior to other clinical signs of infection and are thus desirable to monitor so as to provide timely and efficient treatment.

Illustrative embodiments provide systems that integrate highly sensitive biosensors, such as pH biosensors, with precise and controlled drug delivery to provide point-of-care treatment wherever and whenever treatment is needed. In some embodiments, the integrated biosensor includes a pH biosensor made on a thin and flexible polyimide film suitable for conformal attachment onto wounded skin or another target site of a subject. The integrated pH biosensor may be used for accurate measurement of local changes in pH value. Certain changes in pH value trigger controlled delivery of antibiotics or another drug to a target site (e.g., wounded skin). Drug delivery in some embodiments is designed such that once pH changes detected using the integrated pH biosensor move above a set threshold, or deviate some designated threshold from a previous measurement, an electrical signal is applied to heat a thermally sensitive layer (e.g., tridecanoic) to a temperature above its melting temperature to release drugs from a reservoir to the target site.

Figure 1:
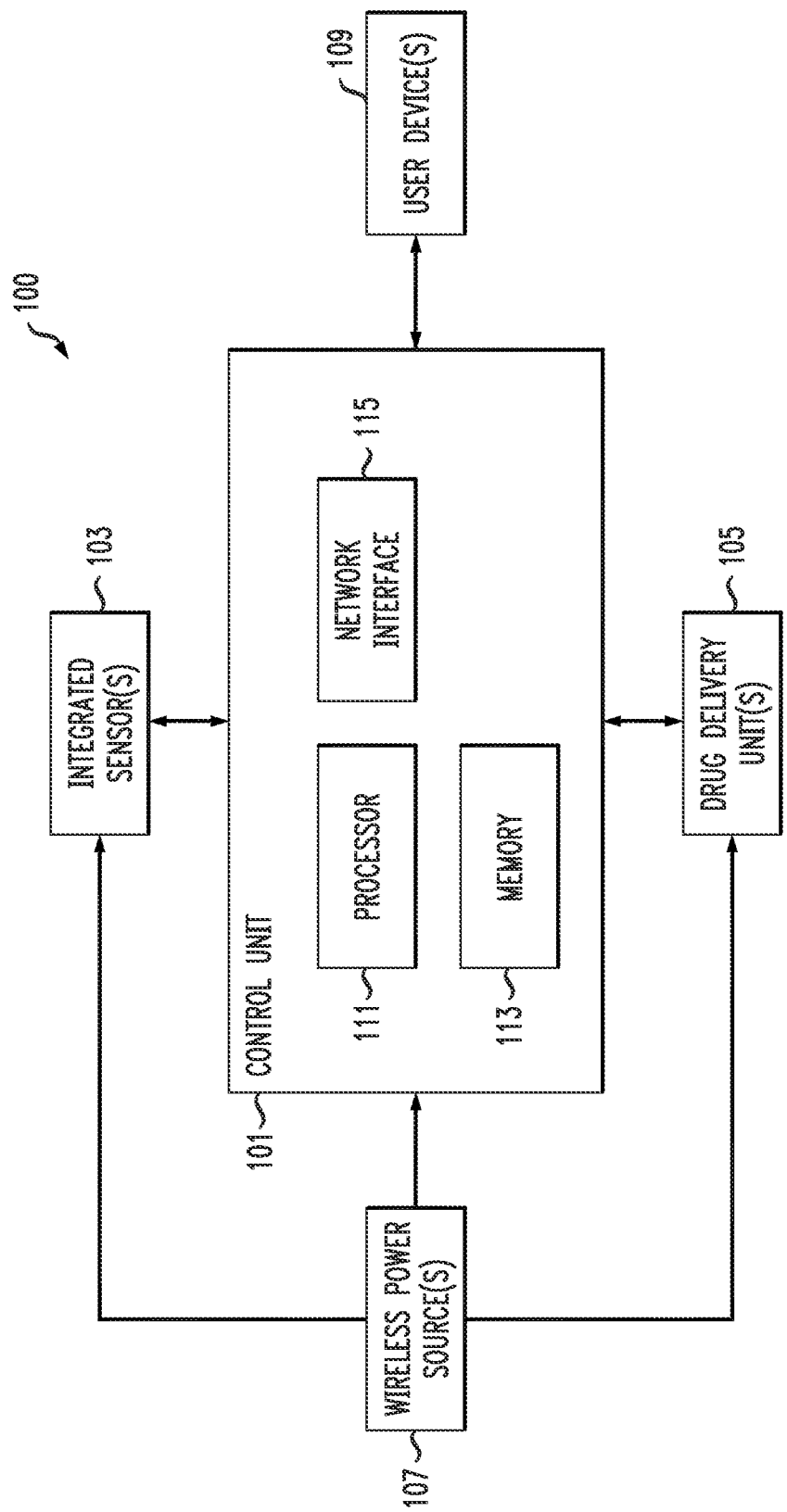
FIG. 1 depicts a point-of-care drug delivery system, according to an embodiment of the present invention.

FIG. 1 shows a point-of-care drug delivery system 100, which includes a control unit 101 coupled to one or more integrated sensors 103 and one or more drug delivery units 105. The control unit 101, integrated sensors 103 and drug delivery units 105 are configured to receive power in some embodiments from one or more wireless power sources 107. For example, the control unit 101, integrated sensors 103 and/or drug delivery units 105 may be implemented as near-field communication (NFC) tags which receive power from an NFC reader (e.g., a wireless power source 107). Various other types of radio frequency (RF) or other wireless power may be used. Further, in some embodiments one or more of the control unit 101, integrated sensors 103 and drug delivery units 105 may include an internal power source such as a battery instead of or in addition to being configured to receive wireless power from wireless power sources 107.

In some embodiments, only one of or a subset of the control unit 101, integrated sensors 103 and drug delivery units 105 may be configured for receiving wireless power. In such embodiments, those elements configured to receive wireless power may provide such power to other elements not configured to receive wireless power. For example, in some embodiments, only the control unit 101 is configured to receive wireless power, with the control unit 101 directing or supplying power to other components such as the integrated sensors 103 and drug delivery units 105.

The control unit 101 includes a processor 111, a memory 113, and a network interface 115. The processor 111 may comprise a microprocessor, a microcontroller, an application-specific integrated circuit (ASIC), a field-programmable gate array (FPGA) or other type of processing circuitry, as well as portions or combinations of such circuitry elements. The memory 113 may comprise random access memory (RAM), read-only memory (ROM) or other types of memory, in any combination. The network interface 115 may include any suitable transceiver or transceivers required for communication with wireless power sources 107 and user devices 109 for a desired communication protocol (e.g., WiFi, Bluetooth, NFC, etc.). The control unit 101 may have appropriate ports or connections to other components such as integrated sensors 103 and drug delivery units 105 as will be described in further detail below.

The control unit 101 may provide feedback to the user devices 109, such as feedback regarding parameters monitored using the integrated sensors 103, amounts of drugs delivered using the drug delivery units 105, etc. The control unit 101 may also be programmed by the user devices 109, so as to adjust thresholds or logic used to control drug delivery via drug delivery units 105 based on parameters monitored using the integrated sensors 103. In some embodiments, one or more of the user devices 109 may provide the wireless power sources 107. The user devices 109 may be, for example, mobile computing devices such as smartphones, tablets, laptops, smartwatches, fitness monitors, etc. The user devices 109 may also be desktop computers, servers, cloud computing systems, etc.

Figure 2:
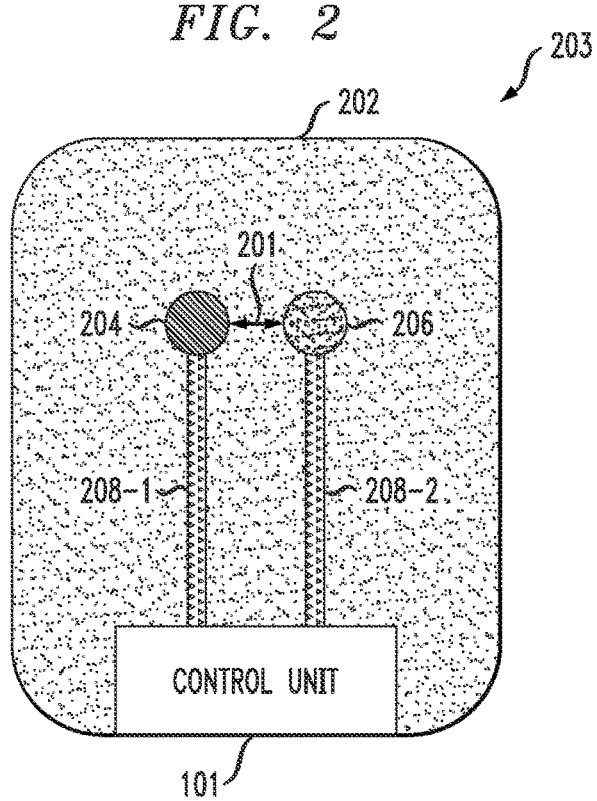
FIG. 2 depicts an example of an integrated sensor for a point-of-care drug delivery system, according to an embodiment of the present invention.

FIG. 2 shows an example of an integrated sensor 203 which may be used as one of the integrated sensors 103 in the point-of-care drug delivery system 100. The integrated sensor 203 includes a substrate 202, which may be formed of polyethylene terephthalate (PET) or another suitable material such as polyimide or silk providing a flexible film for conformal attachment to a target site (e.g., wounded skin). The substrate 202 may have a film thickness in the range of 1 micrometer ($\mu m$) to 500 $\mu m$.

The integrated sensor 203 further includes electrodes 204 and 206. The electrode 204 provides a reference electrode, and the electrode 206 provides an active sensor. In some embodiments, the integrated sensor 203 is a pH sensor, and the reference electrode 204 is formed of silver (Ag), silver chloride (AgCl) or another suitable material such as silver/silver iodide (Ag/AgI), silver/silver sulfide (Ag/Ag$_2$S), etc. The reference electrode 204 may have a surface area in the range of 100 $\mu m^2$ to 10 millimeters squared (mm$^2$). The sensor electrode 206 may be formed of titanium nitride (TiN) or another suitable biocompatible material such as ruthenium nitride (RuN) or aluminum nitride (AlN). The sensor electrode 206 may have a surface area in the range of 100 $\mu m^2$ to 10 mm$^2$. A distance 201 between the reference electrode 204 and the active electrode 206 may be in the range of 10 $\mu m$ to 10 mm.

The integrated sensor 203 may function based on potentiometric measurements of voltage differences between the active electrode 206 and the reference electrode 204. The reference electrode 204 and active electrode 206 are coupled to the control unit 101 as shown using traces 208-1 and 208-2, respectively. The traces 208-1 and 208-2 (collectively, traces 208) may be formed of gold (Au), platinum (Pt), etc. The lengths of the traces 208 may vary as needed based on the layout of the electrodes 204 and 206 and other components of a point-of-care drug delivery system (e.g., control unit 101, drug delivery units 105, etc.). The control unit 101 measures or detects the voltage difference between the active electrode 206 and reference electrode 204, and uses the voltage difference to determine pH or another biological or other parameter of a subject to determine whether to initiate drug delivery via one or more drug delivery elements 105.

Figure 3:
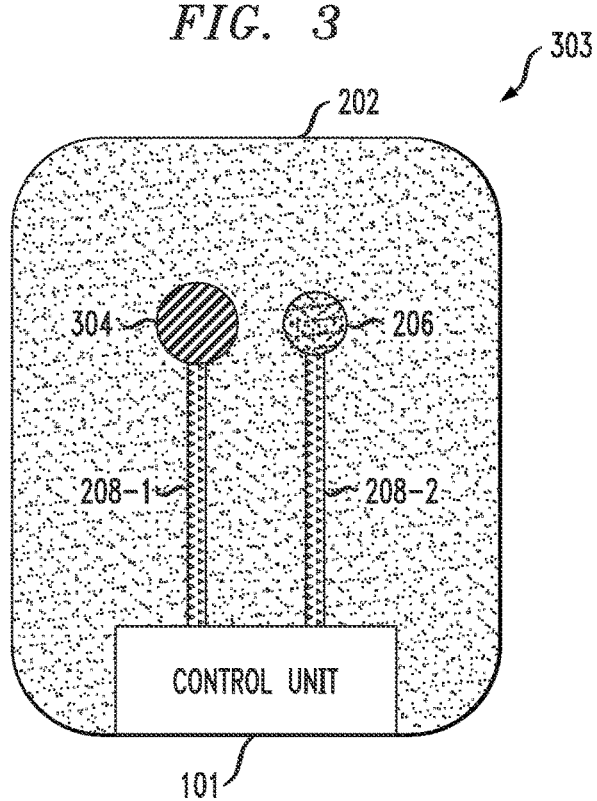
FIG. 3 depicts another example of an integrated sensor for a point-of-care drug delivery system, according to an embodiment of the present invention.

FIG. 3 shows another example of an integrated sensor 303, which is similar to the integrated sensor 203 but includes a polymer-coated reference electrode 304. The polymer-coated reference electrode 304 may be the reference electrode 204 coated with a solid electrolyte, such as a polymer mixed with sodium chloride (NaCl). The polymer may be poly(3,4-ethylenedioxythiophene) polystyrene sulfonate (PEDOT:PSS).

It should be appreciated that although FIGS. 2 and 3 show integrated sensors 203 and 303 each of which includes just one active electrode and one reference electrode, embodiments are not so limited. In some cases, an integrated sensor may include multiple pairs of reference and active electrodes, possibly of different sizes and/or different combinations of materials. Such different pairs of reference and active electrodes may be used to monitor different parameters of a subject (e.g., pH, body temperature, etc.), or to measure a same parameter at different locations. Measurements from different pairs of reference and active electrodes may in some cases be used to trigger drug delivery at different sites via different drug delivery elements 105, to trigger delivery of different drugs at one or more sites via different drug delivery elements 105, etc. Further, in some embodiments multiple active electrodes may be associated or referenced against a same reference electrode, or one active electrode may be associated or referenced against multiple different reference electrodes, etc.

Figure 4A:
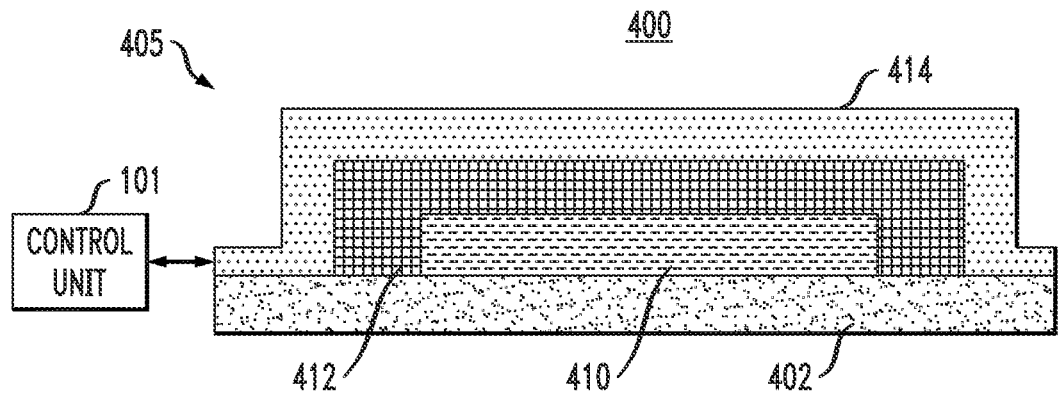
FIG. 4A depicts a cross-sectional view of a drug delivery element for a point-of-care drug delivery system, according to an embodiment of the present invention.
Figure 4B:
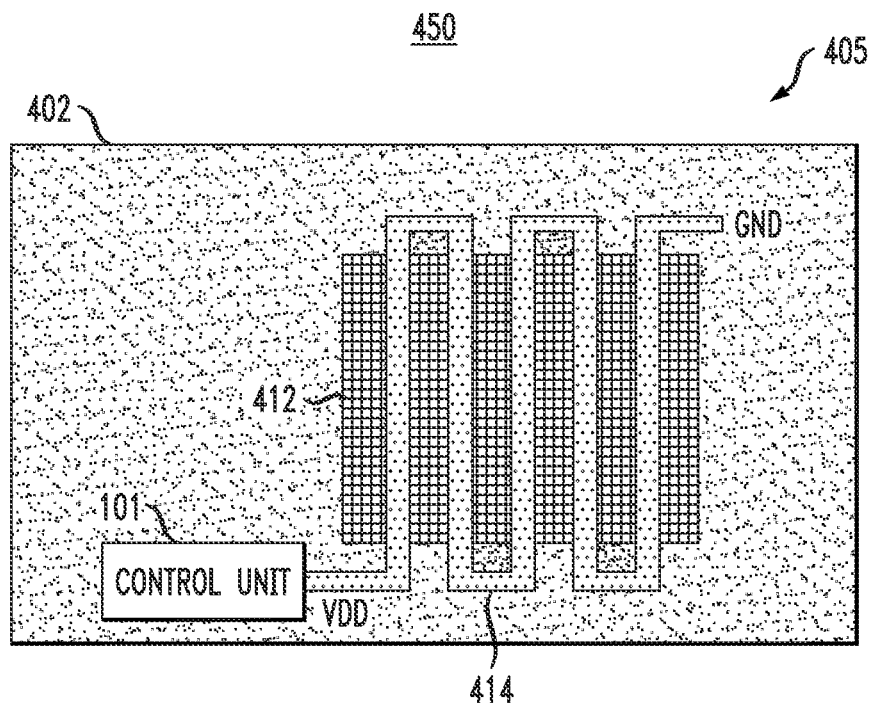
FIG. 4B depicts a top-down view of the FIG. 4A drug delivery element, according to an embodiment of the present invention.

FIG. 4A shows a cross-sectional view 400 of a drug delivery element 405, such as one of the drug delivery elements 105 of point-of-care drug delivery system 100. FIG. 4B depicts a top-down view 450 of the drug delivery element 405. More particularly, the top-down view 450 shows a surface of the drug delivery element 405 that interfaces with the skin of the subject in a target site (e.g., wounded skin).

The drug delivery element 405 includes a substrate 402, which may be formed of similar materials and with similar sizing as that of substrate 202. In some embodiments, the substrate 402 of the drug delivery element 405 may be the same as the substrate 202 of integrated sensor 203/303. In other embodiments, however, the substrates 202 and 402 may be distinct, and may be formed of different materials, with different thickness, etc.

The drug delivery element 405 also includes a reservoir 410 containing a drug, such as an antibiotic or other suitable drug useful for treating one or more conditions detected using the integrated sensors 103. The drug delivery element 405 further includes a thermally active polymer 412 and a heating coil 414.

The thermally active polymer 412 may be formed of poly(N-isopropylacrylamide) (PNIPAAm) or poly(N,N'-diethylacrylamide) (PDEAAm). The thermally active polymer 412 may have a thickness in the range of 100 nanometers (nm) to 100 µm.

The heating coil 414 may be formed of Au, Pt or another suitable material, with a thickness in the range of 50 nm to 1 µm and a width in the range of 1 µm to 1 mm.

On receiving a trigger signal from the control unit 101, the heating coil 414 heats up to metal the thermally active polymer 412, thus releasing the drug contained in reservoir 410. The release of the drug from reservoir 410 may be controlled based on the heating or melting of the thermally active polymer 412. The control unit 101 may provide the trigger signal so as to apply a voltage VDD at one end of the heating coil 414, with the other end of the heating coil 414 being coupled to a ground (GND).

Although FIG. 4 shows a drug delivery unit 405 that includes just one reservoir 410, embodiments are not so limited. In some embodiments, a drug delivery unit 405 may include multiple reservoirs, containing the same or different drugs. For example, the multiple reservoirs may contain a same drug, but be positioned on the substrate 402 so as to interface with different target sites (e.g., wounded skin) of a subject. In such cases, each reservoir may be covered or enclosed by a different portion of the thermally active polymer 412 (or possibly via distinct thermally active polymers), which may be activated or melted via different portions of heating coil 414 (or possibly via distinct heating coils). Two or more reservoirs may alternately be positioned to interface with a same target site (e.g., such as being positioned next to or proximate one another) but contain different drugs so as to provide different treatment to the target site (via the different drugs) based on measurements from the integrated sensors 103. Various other arrangements are possible, including combinations of the above.

Figure 5:
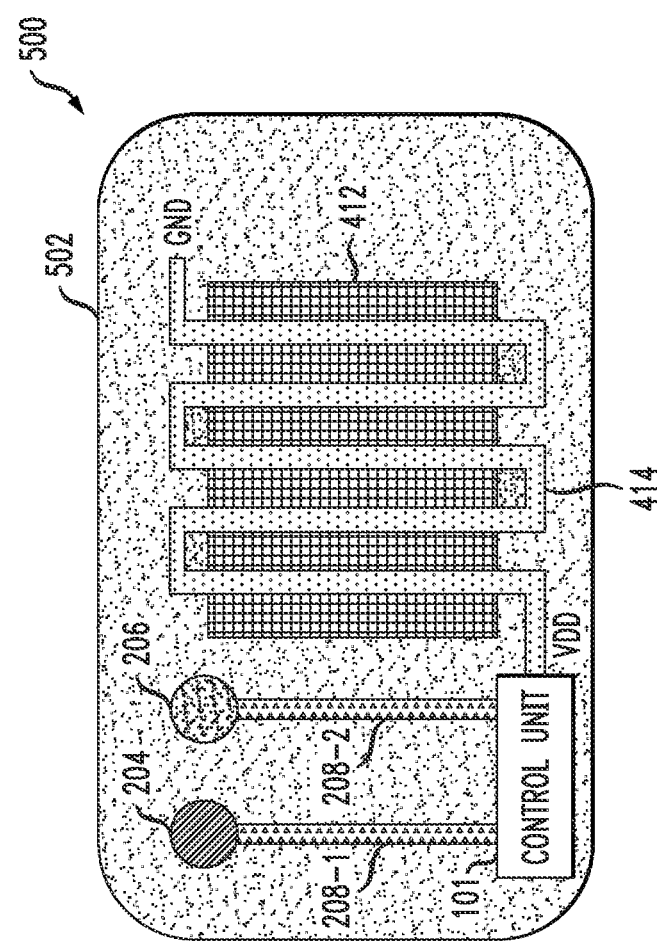
FIG. 5 depicts an integrated sensor and drug delivery unit coupled to a control unit for a point-of-care drug delivery system, according to an embodiment of the present invention.

FIG. 5 shows a point-of-care drug delivery system 500, which includes the integrated sensor 203 and drug delivery unit 405 formed on a common substrate 502. The integrated sensor 203 and drug delivery unit 405 are each coupled to the control unit 101 (e.g., via traces 208 and heating coil 412, respectively).

Figure 6:
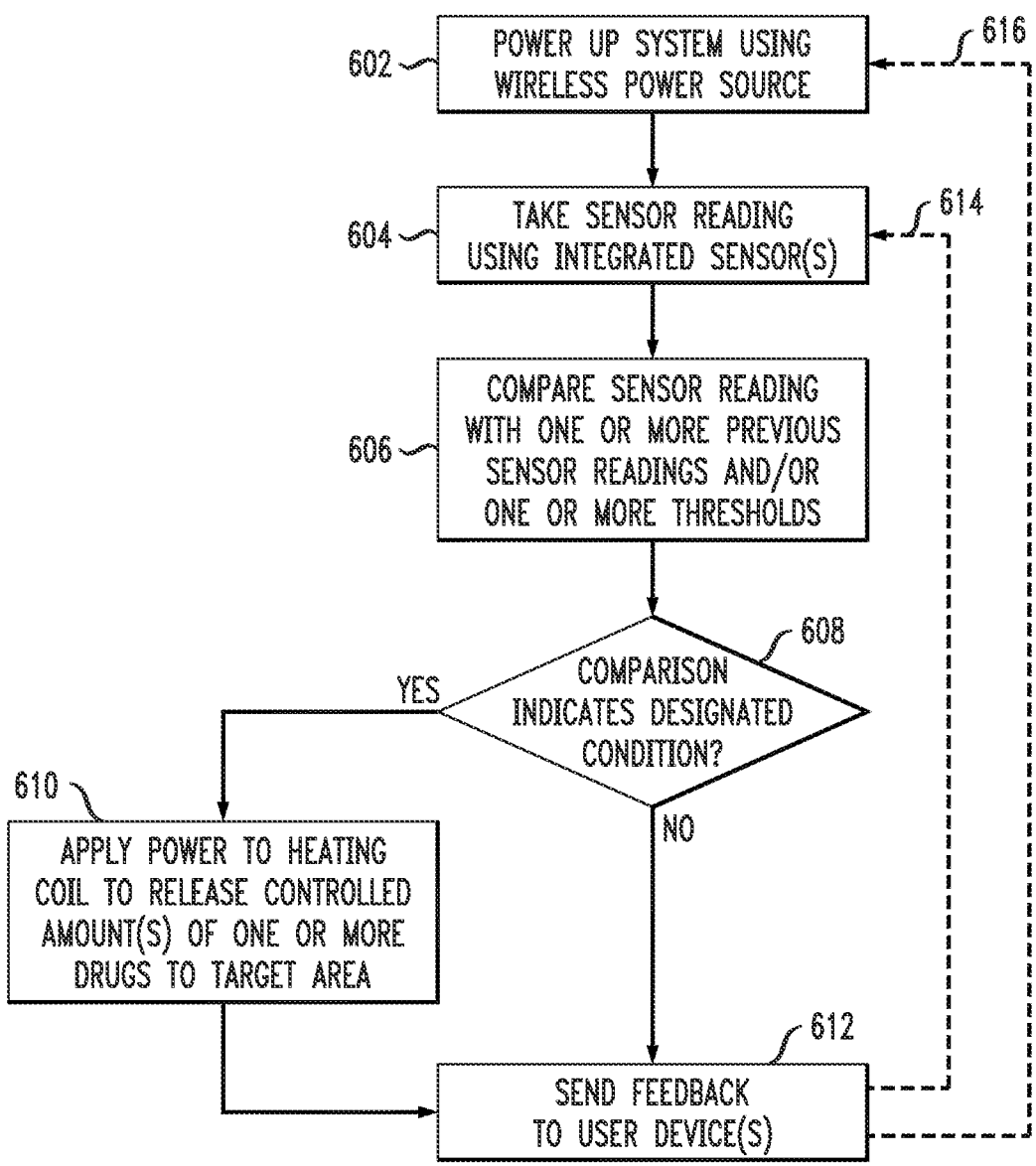
FIG. 6 depicts a process for controlled drug delivery in a point-of-care drug delivery system, according to an embodiment of the present invention.

FIG. 6 depicts a process 600 for controlled drug delivery in a point-of-care drug delivery system such as system 100 or 500. The process 600 begins in step 602 with powering up the point-of-care drug delivery system 100 or 500, such as using a wireless power source 107 (possibly implemented as user device 109 via NFC functionality thereof). In step 604, the control unit 101 takes sensor readings using one or more of the integrated sensors 103. In some embodiments, this includes obtaining sensor readout of the current pH or other biological parameter of a subject at a target site (e.g., a wounded area), which is sent from the integrated sensors 103 to the control unit 101.

In step 606, the control unit 101 compares the sensor reading obtained in step 604 with one or more previous sensor readings, with one or more thresholds, or a combination of both. In some embodiments, this involves comparing a current pH reading with a last (previous) pH reading at the target site and determining whether the pH reading has changed by a designated threshold or otherwise indicates a designated condition (e.g., possible infection).

In step 608, it is determined whether the comparison of step 606 indicates the designated condition. The designated condition may be detected based on the magnitude of the change in pH from the last to the current reading from integrated sensor. The designated condition may also or alternatively be detected based on a threshold pH reading (e.g., a pH above or below a designated threshold, a pH in a designated threshold range, etc.). The particular change in pH from the last to the current reading, or the current value of the pH may be used to control an amount of one or more drugs that are delivered to a target site. For example, the magnitude of pH change (or other biologic parameter) may be related to the degree or severity of a condition (e.g., infection), and thus the amount of drug delivered may be proportional to the detected degree or severity of the designated condition.

If the result of the determination step 608 is yes, or that the designated condition is indicated, the process 600 proceeds with step 610 of applying power to a heating coil (more generally, activating a drug delivery element 105/405) to release a controlled amount of one or more drugs to the target site. Continuing with the above example, if the comparison of the last to the current pH reading indicates infection, heating coils 414 of the drug delivery element 405 are powered up to release a controlled amount of an antibiotic or other suitable drug from reservoir 410 through the thermally active polymer 412.

After step 610, or if the result of the determination step 608 is no, the process 600 proceeds to step 612 of sending feedback to the user devices 109. The feedback may include, by way of example, the current sensor reading (e.g., current pH reading), the amount of drug delivered in step 608, etc. As a result of the feedback, the user devices 109 (or the control unit 101) may initiate one or more of the feedback paths 614, 616. Feedback path 614 includes initiating a new sensor reading and repeating steps 604 through 612. Feedback path 616 includes again powering up the system and repeating steps 602 through 612. One or both of the feedback paths 614 and 616 may further include programming or adjusting logic of a control unit, such as adjusting thresholds for detecting designated conditions, changing which designated conditions are checked for, changing a frequency of measurement by the integrated sensors, etc.

In some embodiments, a drug delivery system comprises a substrate, at least one integrated sensor disposed on the substrate, at least one drug delivery element disposed on the substrate, and a control unit coupled to the at least one integrated sensor and the at least one drug delivery element. The at least one integrated sensor comprises a first electrode disposed on a first surface of the substrate and at least a second electrode disposed on the first surface of the substrate. The at least one drug delivery element comprises a reservoir disposed on the first surface of the substrate, a thermally active polymer enclosing the reservoir and a heating coil disposed over the thermally active polymer. The control unit is configured to measure at least one biological parameter of a subject by measuring a voltage difference between the first electrode and the second electrode of the at least one integrated sensor, and to apply a trigger signal to the heating coil of the at least one drug delivery element responsive to the measured at least one biological parameter indicating a designated condition, the trigger signal heating up the thermally active polymer to selectively release a drug from the reservoir.

The first electrode may comprise a reference electrode and the second electrode may comprise an active sensor electrode. The at least one integrated sensor may comprise a pH sensor and the active sensor electrode may comprise TiN. The reference electrode may comprise one of Ag and AgCl. The reference electrode may alternatively comprise a polymer mixed with a solid electrolyte. The solid electrolyte may comprise NaCl. The drug delivery system may further comprise a first trace coupling the reference electrode to the control unit and a second trace coupling the active sensor electrode to the control unit.

The substrate may comprise a flexible polymer. The flexible polymer may comprise PET.

The heating coil may comprise at least one of Au and Pt.

The control unit may comprise at least one network interface configured to receive wireless power from at least one wireless power source. The at least one network interface may comprise a NFC interface.

In some embodiments, an apparatus comprises a memory and a processor coupled to the memory and configured to measure at least one biological parameter of a subject by measuring a voltage difference between a first electrode and a second electrode of at least one integrated sensor disposed on a substrate, and to apply a trigger signal to a heating coil of at least one drug delivery element disposed on the substrate responsive to the measured at least one biological parameter indicating a designated condition, the trigger signal heating up a thermally active polymer of the at least one drug delivery element that encloses a reservoir to selectively release a drug from the reservoir.

In some embodiments, a method for controlled drug delivery comprises measuring at least one biological parameter of a subject by measuring a voltage difference between a first electrode and a second electrode of at least one integrated sensor disposed on a substrate, and applying a trigger signal to a heating coil of at least one drug delivery element disposed on the substrate responsive to the measured at least one biological parameter indicating a designated condition, the trigger signal heating up a thermally active polymer of the at least one drug delivery element that encloses a reservoir to selectively release a drug from the reservoir. The method is performed by a control unit comprising a processor coupled to a memory.

The method may further comprise applying wireless power to the control unit using NFC functionality of a user device in wireless communication with the control unit.

The at least one integrated sensor may comprise a pH sensor, and measuring the at least one biological parameter of the subject may comprise obtaining a sensor readout of a current pH of a target site of the subject. The method may further comprise comparing the current pH of the target site of the subject with at least one previous sensor readout of the pH of the target site of the subject to determine whether the designated condition is present. Applying the trigger signal heats up the thermally active polymer to release a controlled amount of the drug from the reservoir to the target site of the subject. The controlled amount of the drug is determined based on the current pH of the target site of the subject.

Embodiments of the present invention include a system, a method, and/or a computer program product at any possible technical detail level of integration. The computer program product may include a computer readable storage medium (or media) having computer readable program instructions thereon for causing a processor to carry out aspects of the present invention. For example, the memory 113 of control unit 101 may be viewed as a computer readable storage medium carrying program instructions for causing processor 111 to perform the process 600 or other functionality described herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
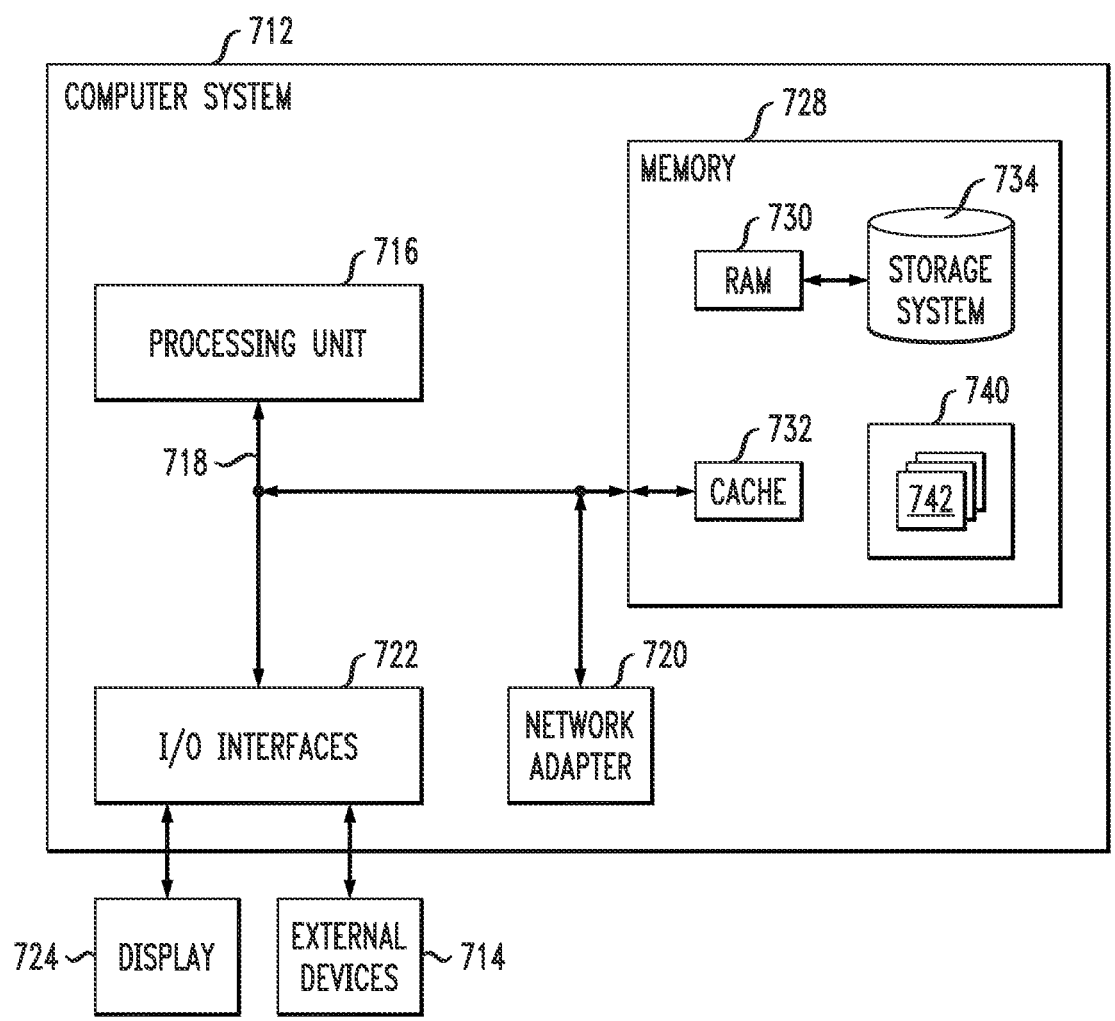
FIG. 7 depicts a computer system in accordance with which one or more components/steps of techniques of the invention may be implemented, according to an exemplary embodiment of the invention.

One or more embodiments can make use of software running on a general-purpose computer or workstation. By way of example, the control unit 101 or user devices 109 may be implemented at least in part using software running on a general-purpose computer or workstation. With reference to FIG. 7, in a computing node 710 there is a computer system/server 712, which is operational with numerous other general purpose or special purpose computing system environments or configurations. Examples of well-known computing systems, environments, and/or configurations that may be suitable for use with computer system/server 712 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, mobile and wearable devices, and distributed cloud computing environments that include any of the above systems or devices, and the like.

Computer system/server 712 may be described in the general context of computer system executable instructions, such as program modules, being executed by a computer system. Generally, program modules may include routines, programs, objects, components, logic, data structures, and so on that perform particular tasks or implement particular abstract data types. Computer system/server 712 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 712 in computing node 710 is shown in the form of a general-purpose computing device. The components of computer system/server 712 may include, but are not limited to, one or more processors or processing units 716, a system memory 728, and a bus 718 that couples various system components including system memory 728 to processor 716.

The bus 718 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 712 typically includes a variety of computer system readable media. Such media may be any available media that is accessible by computer system/server 712, and it includes both volatile and non-volatile media, removable and non-removable media.

The system memory 728 can include computer system readable media in the form of volatile memory, such as random access memory (RAM) 730 and/or cache memory 732. The computer system/server 712 may further include other removable/non-removable, volatile/nonvolatile computer system storage media. By way of example only, storage system 734 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 718 by one or more data media interfaces. As depicted and described herein, the memory 728 may include at least one program product having a set (e.g., at least one) of program modules that are configured to carry out the functions of embodiments of the invention. A program/utility 740, having a set (at least one) of program modules 742, may be stored in memory 728 by way of example, and not limitation, as well as an operating system, one or more application programs, other program modules, and program data. Each of the operating system, one or more application programs, other program modules, and program data or some combination thereof, may include an implementation of a networking environment. Program modules 742 generally carry out the functions and/or methodologies of embodiments of the invention as described herein.

Computer system/server 712 may also communicate with one or more external devices 714 such as a keyboard, a pointing device, a display 724, etc., one or more devices that enable a user to interact with computer system/server 712, and/or any devices (e.g., network card, modem, etc.) that enable computer system/server 712 to communicate with one or more other computing devices. Such communication can occur via I/O interfaces 722. Still yet, computer system/server 712 can communicate with one or more networks such as a LAN, a general WAN, and/or a public network (e.g., the Internet) via network adapter 720. As depicted, network adapter 720 communicates with the other components of computer system/server 712 via bus 718. It should be understood that although not shown, other hardware and/or software components could be used in conjunction with computer system/server 712. Examples include, but are not limited to, microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
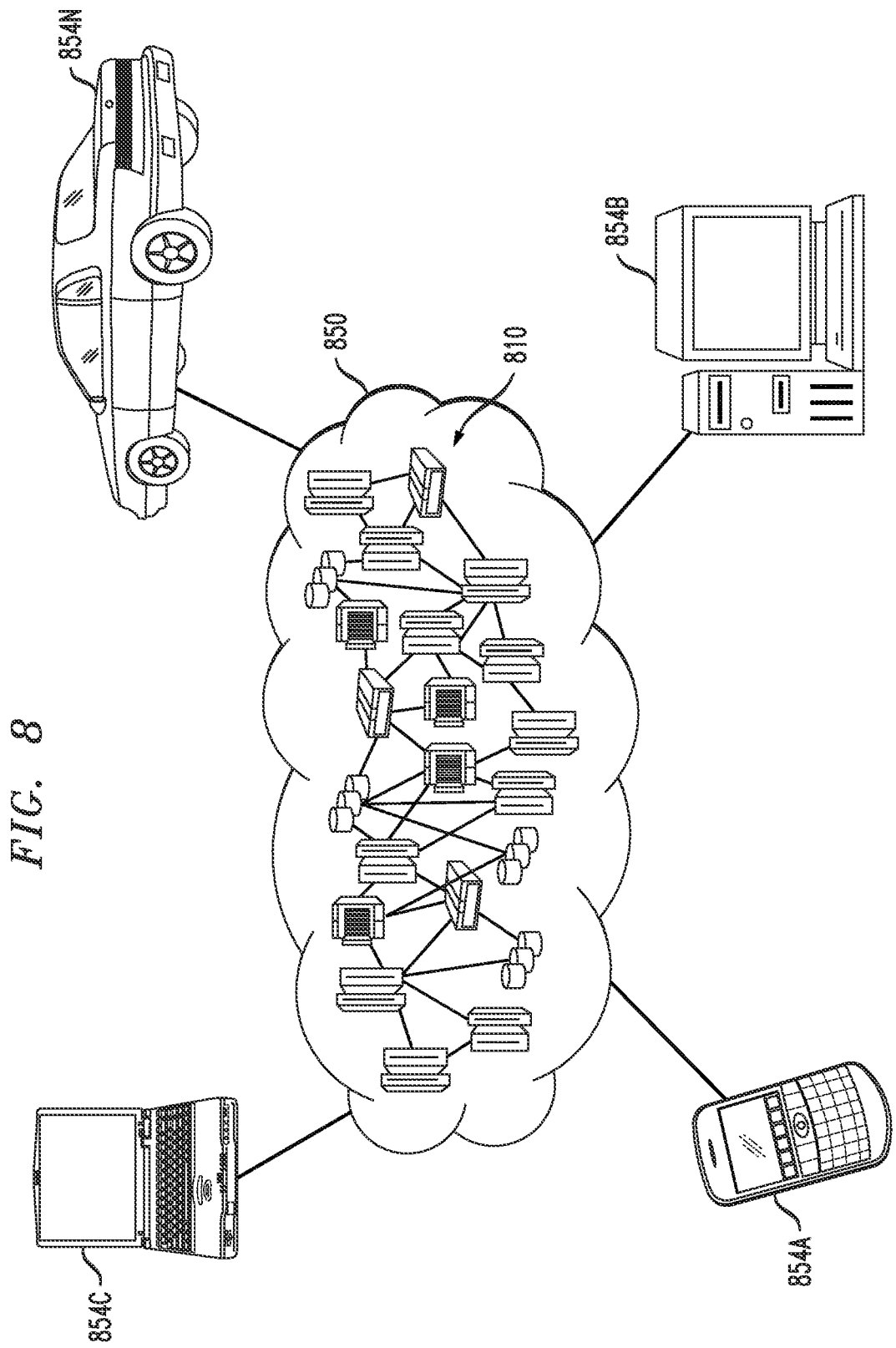
FIG. 8 depicts a cloud computing environment, according to an exemplary embodiment of the present invention.

Referring now to FIG. 8, illustrative cloud computing environment 850 is depicted. As shown, cloud computing environment 850 includes one or more cloud computing nodes 810 with which local computing devices used by cloud consumers, such as, for example, personal digital assistant (PDA) or cellular telephone 854A, desktop computer 854B, laptop computer 854C, and/or automobile computer system 854N may communicate. Nodes 810 may communicate with one another. They may be grouped (not shown) physically or virtually, in one or more networks, such as Private, Community, Public, or Hybrid clouds as described hereinabove, or a combination thereof. This allows cloud computing environment 850 to offer infrastructure, platforms and/or software as services for which a cloud consumer does not need to maintain resources on a local computing device. It is understood that the types of computing devices 854A-N shown in FIG. 8 are intended to be illustrative only and that computing nodes 810 and cloud computing environment 850 can communicate with any type of computerized device over any type of network and/or network addressable connection (e.g., using a web browser).

Figure 9:
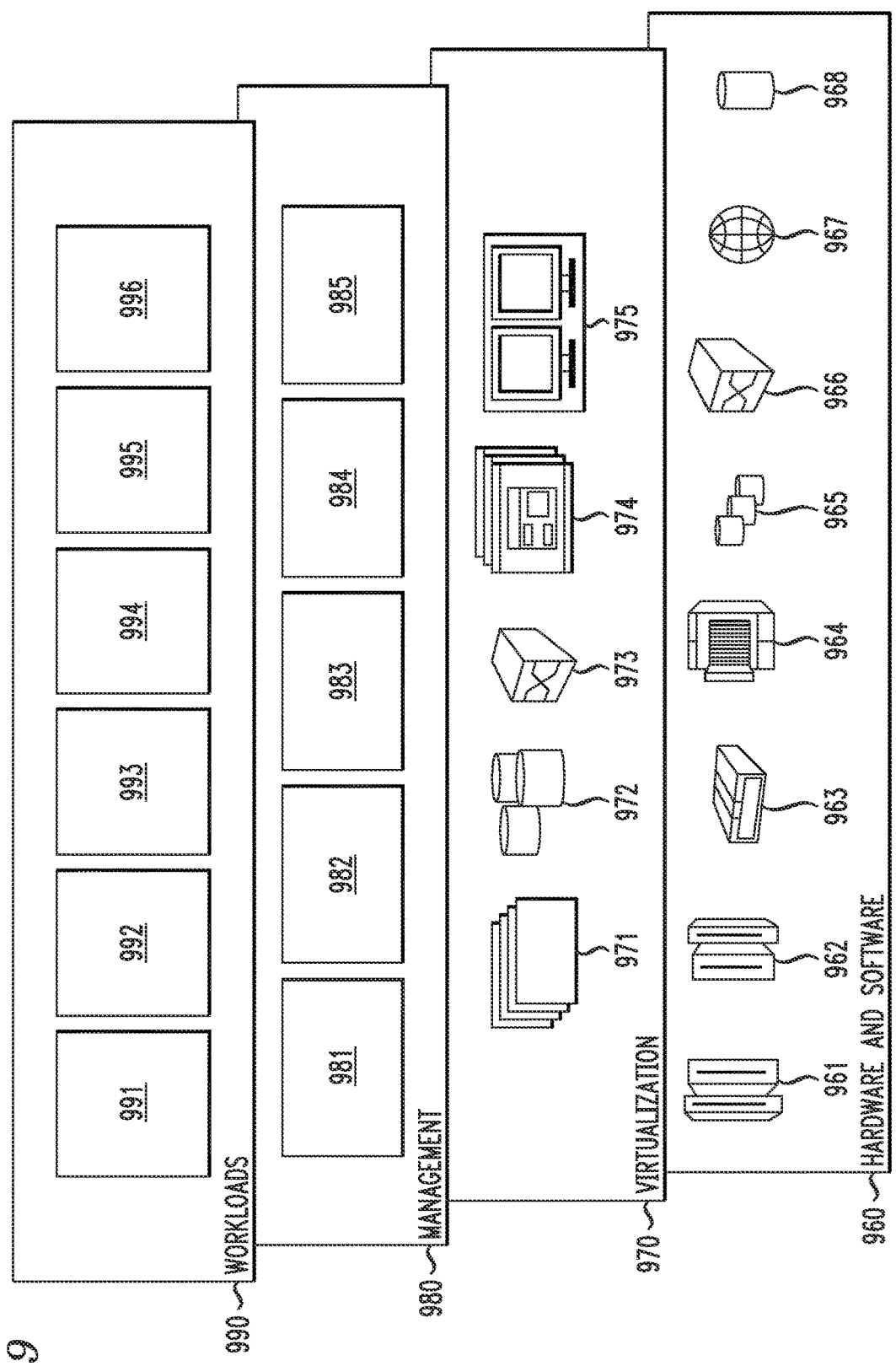
FIG. 9 depicts abstraction model layers, according to an exemplary embodiment of the present invention.

Referring now to FIG. 9, a set of functional abstraction layers provided by cloud computing environment 850 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 960 includes hardware and software components. Examples of hardware components include: mainframes 961; RISC (Reduced Instruction Set Computer) architecture based servers 962; servers 963; blade servers 964; storage devices 965; and networks and networking components 966. In some embodiments, software components include network application server software 967 and database software 968.

Virtualization layer 970 provides an abstraction layer from which the following examples of virtual entities may be provided: virtual servers 971; virtual storage 972; virtual networks 973, including virtual private networks; virtual applications and operating systems 974; and virtual clients 975.

In one example, management layer 980 may provide the functions described below. Resource provisioning 981 provides dynamic procurement of computing resources and other resources that are utilized to perform tasks within the cloud computing environment. Metering and Pricing 982 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 983 provides access to the cloud computing environment for consumers and system administrators. Service level management 984 provides cloud computing resource allocation and management such that required service levels are met. Service Level Agreement (SLA) planning and fulfillment 985 provide pre-arrangement for, and procurement of, cloud computing resources for which a future requirement is anticipated in accordance with an SLA.

Workloads layer 990 provides examples of functionality for which the cloud computing environment may be utilized. Examples of workloads and functions which may be provided from this layer include: mapping and navigation 991; software development and lifecycle management 992; virtual classroom education delivery 993; data analytics processing 994; transaction processing 995; and drug delivery management processing 996, which may perform various functions for managing point-of-care drug delivery utilizing system described herein. Such management may include programming of control units of one or more point-of-care drug delivery systems, coordinating gathering of information from control units of one or more point-of-care drug delivery systems, etc. Such management may also include directing control of drug delivery elements of point-of-care drug delivery systems via control units thereof, providing wireless power to point-of-care drug delivery systems, managing a set of multiple point-of-care drug delivery systems, etc.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A drug delivery system, comprising:
   a substrate;
   at least one network interface configured to receive wireless power from at least one wireless power source;
   at least one integrated sensor disposed on the substrate, the at least one integrated sensor comprising a first electrode disposed on a first surface of the substrate and at least a second electrode disposed on the first surface of the substrate;
   at least one drug delivery element disposed on the substrate, the at least one drug delivery element comprising a reservoir disposed on the first surface of the substrate, a thermally active polymer enclosing the reservoir and a heating coil disposed over the thermally active polymer; and
   a control unit coupled to the at least one network interface, the at least one integrated sensor and the at least one drug delivery element, the control unit being configured:
      to receive wireless power from a user device providing the at least one wireless power source;
      to supply at least a portion of the received wireless power from the user device providing the at least one wireless power source to at least one of the at least one integrated sensor and the at least one drug delivery element;

to measure at least one biological parameter of a subject by measuring a voltage difference between the first electrode and the second electrode of the at least one integrated sensor;

to determine whether the measured at least one biological parameter indicates a designated condition;

responsive to the measured at least one biological parameter indicating the designated condition, to identify a severity of the designated condition based at least in part on a magnitude of a change of the measured at least one biological parameter from one or more previous measurements of the at least one biological parameter;

to apply a trigger signal to the heating coil of the at least one drug delivery element responsive to the measured at least one biological parameter indicating the designated condition, the trigger signal heating up the thermally active polymer to selectively release a designated amount of a drug from the reservoir, the designated amount of the drug being controlled based at least in part on the identified severity of the designated condition;

to provide feedback to the user device providing the at least one wireless power source, the feedback comprising at least one of a current reading of the at least one integrated sensor and an amount of the drug selectively released from the reservoir; and to receive, from the user device providing the at least one wireless power source, an instruction to modify one or more thresholds for detecting the designated condition;

wherein the first electrode comprises a reference electrode and the second electrode comprises an active sensor electrode; and wherein the at least one integrated sensor comprises a pH sensor and the active sensor electrode comprises titanium nitride (TiN).

2. The system of claim 1, wherein the reference electrode comprises one of silver (Ag) and silver chloride (AgCl).

3. The system of claim 1, wherein the reference electrode is coated with a solid electrolyte.

4. The system of claim 3, wherein the solid electrolyte comprises a polymer mixed with sodium chloride (NaCl).

5. The system of claim 1, further comprising a first trace coupling the reference electrode to the control unit and a second trace coupling the active sensor electrode to the control unit.

6. The system of claim 1, wherein the substrate comprises a flexible polymer.

7. The system of claim 6, wherein the flexible polymer comprises polyethylene terephthalate (PET).

8. The system of claim 1, wherein the thermally active polymer comprises at least one of poly(N-isopropylacrylamide) (PNIPAAm) and poly(N,N'-diethylacrylamide) (PDEAAm).

9. The system of claim 1, wherein the heating coil comprises at least one of gold and platinum.

10. The system of claim 1, wherein the at least one network interface comprises a near-field communication (NFC) interface.

11. The system of claim 1, wherein the control unit is further configured to receive, from the user device providing the at least one wireless power source, an instruction to modify a frequency of measurement of the at least one biological parameter.

12. The system of claim 1, wherein the control unit is further configured to receive, from the user device providing the at least one wireless power source, an instruction to detect at least one additional condition using the measurement of the at least one biological parameter.

13. An apparatus comprising:
at least one network interface configured to receive wireless power from at least one wireless power source;
a memory; and
a processor coupled to the memory and the at least one network interface, the processor being configured:
to receive wireless power from a user device providing the at least one wireless power source;
to supply at least a portion of the received power from the user device providing the at least one wireless power source to at least one of at least one integrated sensor disposed on a substrate and at least one drug delivery element disposed on the substrate;
to measure at least one biological parameter of a subject by measuring a voltage difference between a first electrode and a second electrode of the at least one integrated sensor;
to determine whether the measured at least one biological parameter indicates a designated condition;
responsive to the measured at least one biological parameter indicating the designated condition, to identify a severity of the designated condition based at least in part on a magnitude of a change of the measured at least one biological parameter from one or more previous measurements of the at least one biological parameter;
to apply a trigger signal to a heating coil of the at least one drug delivery element responsive to the measured at least one biological parameter indicating the designated condition, the trigger signal heating up the thermally active polymer to selectively release a designated amount of a drug from the reservoir, the designated amount of the drug being controlled based at least in part on the identified severity of the designated condition;
to provide feedback to the user device providing the at least one wireless power source, the feedback comprising at least one of a current reading of the at least one integrated sensor and an amount of the drug selectively released from the reservoir; and
to receive, from the user device providing the at least one wireless power source, an instruction to modify one or more thresholds for detecting the designated condition;
wherein the first electrode comprises a reference electrode and the second electrode comprises an active sensor electrode; and
wherein the at least one integrated sensor comprises a pH sensor and the active sensor electrode comprises titanium nitride (TiN).

14. The apparatus of claim 13, wherein the at least one network interface comprises a near-field communication (NFC) interface.

15. A method for controlled drug delivery, comprising:
receiving, via at least one network interface, wireless power from a user device providing at least one wireless power source;
supplying at least a portion of the received wireless power from the user device providing the at least one wireless power source to at least one of at least one integrated sensor disposed on a substrate and at least one drug delivery element disposed on the substrate;

measuring at least one biological parameter of a subject by measuring a voltage difference between a first electrode and a second electrode of the at least one integrated sensor;

determining whether the measured at least one biological parameter indicates a designated condition;

responsive to the measured at least one biological parameter indicating the designated condition, identifying a severity of the designated condition based at least in part on a magnitude of a change of the measured at least one biological parameter from one or more previous measurements of the at least one biological parameter;

applying a trigger signal to a heating coil of the at least one drug delivery element responsive to the measured at least one biological parameter indicating the designated condition, the trigger signal heating up a thermally active polymer of the at least one drug delivery element that encloses a reservoir to selectively release a designated amount of a drug from the reservoir, the designated amount of the drug being controlled based at least in part on the identified severity of the designated condition;

providing feedback to the user device providing the at least one wireless power source, the feedback comprising at least one of a current reading of the at least one integrated sensor and an amount of the drug selectively released from the reservoir; and receiving, from the user device providing the at least one wireless power source, an instruction to modify one or more thresholds for detecting the designated condition;

wherein the first electrode comprises a reference electrode and the second electrode comprises an active sensor electrode;

wherein the at least one integrated sensor comprises a pH sensor and the active sensor electrode comprises titanium nitride (TiN); and wherein the method is performed by a control unit comprising a processor coupled to a memory.

16. The method of claim 15, wherein receiving the wireless power comprises utilizing near-field communication (NFC) functionality of the user device in wireless communication with the control unit.

17. The method of claim 15, wherein the at least one integrated sensor comprises a pH sensor, and wherein measuring the at least one biological parameter of the subject comprises obtaining a sensor readout of a current pH of a target site of the subject.

18. The method of claim 17, further comprising comparing the current pH of the target site of the subject with at least one previous sensor readout of the pH of the target site of the subject to determine whether the designated condition is present.

19. The method of claim 18, wherein applying the trigger signal heats up the thermally active polymer to release a controlled amount of the drug from the reservoir to the target site of the subject.

20. The method of claim 19, wherein the controlled amount of the drug is determined based on the current pH of the target site of the subject.

* * * * *